(12) United States Patent
Vercauteren et al.

(10) Patent No.: US 6,572,882 B1
(45) Date of Patent: Jun. 3, 2003

(54) COMPOSITIONS BASED ON RESVERATROL

(75) Inventors: Joseph Vercauteren, Pessac (FR);
Chantal Castagnino, Merignac (FR);
Jean-Claude Delaunay, Merignac (FR)

(73) Assignee: Caudalie, Paris (FR)

( * ) Notice: Subject to any disclaimer, the term of this patent is extended or adjusted under 35 U.S.C. 154(b) by 0 days.

(21) Appl. No.: 09/462,778
(22) PCT Filed: Jul. 15, 1998
(86) PCT No.: PCT/FR98/01548
§ 371 (c)(1),
(2), (4) Date: Jan. 19, 2000
(87) PCT Pub. No.: WO99/03816
PCT Pub. Date: Jan. 28, 1999

(30) Foreign Application Priority Data

Jul. 15, 1997 (FR) .............................. 97 08964

(51) Int. Cl.⁷ .............................. A01N 43/16
(52) U.S. Cl. .................. 424/451; 424/489; 514/733; 514/734
(58) Field of Search .............. 514/733, 734; 424/489, 451

(56) References Cited

FOREIGN PATENT DOCUMENTS

| EP | 0 773 020 A3 | 5/1997 |
|----|--------------|--------|
| JP | 360009455 | * 1/1985 |
| JP | 61171427 | * 8/1986 |

OTHER PUBLICATIONS

Gromova et al. Stillbenes of the outer bark of Pinus sibrica and Piceas Koraiensis. Khim. Prir. Soedin. vol. 2, pp. 275–6. 1997.*

Chemical Abstracts, vol. 60, No. 4, Feb. 17, 1964, Columbus, Ohio, US: abstract No. 4240c, Susumu Nonomura et al: "Chemical constituents of polygonaceous plants.I.Components of Polygonum cuspidatum", col. 4240 and Susumu Nonomura et al; Yakugaku Zasshi, vol. 83, 1963, pp. 988–990, Japan.

Jang et al., "Cancer Chemopreventive Activity of Resveratrol, a Natural Product Derived from Grapes", Science, vol. 275, pp. 218–220, Jan. 10, 1997.

* cited by examiner

*Primary Examiner*—Thurman K. Page
*Assistant Examiner*—Lakshmi Channavajjala
(74) *Attorney, Agent, or Firm*—Nixon & Vanderhye P.C.

(57) ABSTRACT

The invention relates to compositions based on derivatives of resveratrol having in particular a high stability as regards air and light.

15 Claims, 5 Drawing Sheets

COMPOSITIONS BASED ON RESVERATROL

The present application is a 371 PCT/FR 98/01548, filed Jul. 15, 1998.

The invention relates to compositions based on derivatives of resveratrol having in particular a high stability as regards air and light.

Resveratrol (3,5,4'-trihydroxystilbene) exists in cis or trans form and is presented in monomer form or as the oligomer containing generally 2 to 4 monomer units.

In the following description and in the claims, the term "ORs" will be used to designate both the monomer and the oligomers.

Study of the properties of resveratrol has allowed the demonstration of useful biological activities. Cardiovascular and anti-carcinogenic effects have thus been reported.

The practical use of ORs is hindered by difficult access, selectively, to such extracts, from plant sources which contain them. It is also due to their instability, caused by the phenol groups which they contain, and to their hydrosoluble character, which poses miscibility problems with numerous excipients generally used in therapeutics, cosmetics and in the field of foods, which on the contrary have liposoluble properties.

In order to resolve these problems, the inventors have perfected extraction methods leading to extracts which are rich in ORs, and have used protective groups of the phenol functions, which allow both a satisfactory stability to be conferred on the resveratrol monomer and oligomer and renders them liposoluble, these groups having the advantage of being eliminable in vivo.

Therefore an aim of the invention is to provide compositions based on derivatives of resveratrol monomers and/or oligomers the protective groups of which can be easily eliminated in order to release the active ingredient when desired.

It also aims to provide a process for obtaining these compositions as well as the starting monomers and/or oligomers.

Moreover the invention relates to uses of these compositions in various fields in particular in therapeutics, in cosmetics and in agro-foodstuffs.

The compositions according to the invention are characterized in that they are essentially based on esters of resveratrol monomers and/or oligomers, the monomers comprising at least one ester group of formula —O—CO—A, and the oligomers being formed from monomer units joined by carbon-carbon bonds, or ether, and/or monomers cross-linked by O—CO—R—CO— groups A representing an alkyl radical with at least two carbon atoms, linear or branched, saturated or unsaturated, an aryl radical, except for the phenyl radical in the case of a composition of resveratrol monomer, aralkyl or aralkylene, and R representing an alkylene radical with 0 to 10 carbon atoms, saturated or unsaturated, and/or 1 arylene radical having 1 to 3 rings and/or a heterocyclic radical, and the diastereoisomers of these units.

These compositions can be stored over a long period without alteration, in particular for at least 2 years under normal storage conditions (temperature of 10 to 22° C., in light protective packaging, hygrometry 40–50%).

In an embodiment of the invention, the compositions are based on monomers and/or oligomers of resveratrol comprising at least one —O—CO—A group.

In a preferred group, A represents a saturated or unsaturated fatty acid radical.

In the case of an unsaturation, the double bonds are advantageously cis, which corresponds to the most frequent case found in the natural products. With products obtained more particularly by synthesis or hemisynthesis, the bonds are trans.

Among the fatty acids which are suitable for the implementation of the invention, the following acids can be mentioned: butyric C4:O; valeric, C'5:O hexanoic, C6:O: sorbic, C6:2(n-2); lauric C12:O; palmitic C16:O; stearic, C18:O; oleic, C18:1(n-9) linoleic, C18:2(n-6); linolenic, C18:3(n-6); α linolenic, C18:3(n-3); arachidonic, C20:4(n-3) eicosapentaenoic C20:5(n-3); and docosahexanoic. C22:6 (n-3)

The C16 and more fatty acids are particularly appropriate as regards cosmetic uses. These fatty acids are extracted, for example, from microalgae.

In another preferred group, A represents an aryl group, except for, as specified above, the phenyl radical in the case of a composition of resveratrol monomer.

In yet another group, A represents an aralkyl or aralkylene group, the alkyl or alkylene group being more particularly C1 to C8, in particular C1 to C4. In particular the benzyl or styryl group can be mentioned.

In another embodiment of the invention, the compositions are based on monomers and/or of oligomers of resveratrol cross-linked using —O—CO—R—CO— bridges.

In this structure, R represents an alkylene radical with 0 to 10 carbon atoms, saturated or unsaturated, and/or an arylene radical comprising 1 to 3 rings and/or a heterocyclic radical.

The cross-linked esters advantageously include as substituent R, a radical of a diacid chosen from the following acids: malic, malonic, glutaric, phthalic, a chloride of diacids, such as terephthaloyl dichloride, succinyl dichloride, sebacoyl dichloride, and adipoyl dichloride, an anhydride, or also an isocyanate such as toluene or hexamethylene diisocyanate.

In an advantageous manner, these cross-linked compositions form microcapsules or spongy masses.

The invention also relates to a process for obtaining the esters defined above.

This process is characterized in that it comprises the reaction of monomers and/or of oligomers of resveratrol with, as acylation agents, compounds of formula A—CO—O-A1, or A1-O—CO—R—CO—O-A1, where A represents an alkyl radical with at least two carbon atoms, linear or branched, saturated or unsaturated, an aryl, aralkyl or aralkylene radical, R represents an alkylene radical with 0 to 10 carbon atoms, saturated or unsaturated, and/or 1 arylene radical having 1 to 3 rings and/or a heterocyclic radical, and A1 represents a hydrogen atom, a halogen atom, a C1 to C8 alkyl radical, or aryl, a —CO—A group or isocyanate, A and A1 not being able to represent a phenyl radical and a chlorine atom in A—CO—C-A1.

The esterification reactions with acids are generally carried out at ambient temperature, in the presence of an activation agent. For example dicyclohexylcarbodiimide (DCC) or ter-butylchloroformiate can be mentioned.

The esterifications with acid derivatives are advantageously carried out according to the Schotten Baumann reaction in alkaline aqueous medium.

These reactions lead to the obtaining of esterified compositions in spongy form, which are isolated from the reaction mixture and which are purified with a view to the subsequent uses envisaged.

When diacids or their derivatives are used, an emulsion of (W/O) type is formed by dispersion, under agitation, of an alkaline aqueous solution of the monomers and/or oligomers of resveratrol in an organic solvent which is not miscible with water, then the cross-linking agent, A1-O—CO—R—CO—O-A1 in solution in said non-miscible organic solvent is added, or, as a variant, an emulsion of (O/W) type is formed by dispersion, under agitation, of an organic solution containing said cross-linking agent in an aqueous solution of monomers and/or oligomers of resveratrol, with an alkaline agent in aqueous solution added to it to adjust the pH of the dispersing phase to approximately 9–11.5.

The emulsifying agents are used at the rate of approximately 2 to 15% by weight, relative to the weight of the dispersion, in particular approximately 3 to 8%.

The appropriate agents correspond to those usually used, such as those marketed under the mark Spans® (esterified hexyl alcohols) or Tween® (esters of fatty acids and sorbitol with ethylene oxide).

Depending on the relative quantities of the aqueous and organic phases and of the emulsifying agent, an emulsion of O/W or W/O type is formed.

Agitation is carried out so as to rapidly homogenize the aqueous and organic solutions, for example by using a magnetic stirrer at 500–1000 rpm or a helix at 800–2000 rpm. The duration of this stage is generally of the order of 30 minutes.

The cross-linking occurs se product at the interface of the droplets of the emulsion.

The cross-linked esters formed are recovered, for example by centrifugation. The washed and dried products are in the form of fluid powder.

The esters formed can also be recovered by dilution of the reaction mixture using one or more solvents, decantation and/or centrifugation, and washing.

Observation by microscope shows that the droplets are in the form of approximately spherical particles, with a homogeneous size.

Their diameter can vary from approximately 25 to 300$\mu$ according to the conditions used for obtaining them.

In the case of microcapsules containing the active ingredients, the latter is preferably added to the aqueous or organic phase in which they are soluble.

The monomers and/or oligomers of resveratrol, abbreviated to ORs, used in the esterification stage can be obtained from various plant sources. Vitaceae, Umbelliferae, Myrtaceae, Dipterocarpaceae, Cyperaceae, Gnetaceae, Leguminosae, Gramineae, Sericeae, Haemodoraceae Musaceae, Polygonaceae, Pinaceae, Cupressaceae, Cesalpiniaceae, Poaceae, and Solanaceae can be mentioned.

In an advantageous manner, monomers and/or oligomers of resveratrol are used such as those obtained by extraction, using water and/or of an organic solvent, from vine stalks.

The process for obtaining monomers and oligomers of resveratrol, which is also envisaged by the invention, comprises the following stages extraction by addition, to the vine stalks, of water and/or of organic solvent(s), by subjecting the whole to a treatment such as maceration/lixiviation, ultrasonics or microwaves, delipidation before or after the extraction stage using a solvent of petroleum ether, hexane or chloroform type, additional extraction of the extract recovered by an organic solvent of ethyl acetate or ethyl ether type, concentration of the crude extract obtained, and, if desired, its lyophilization.

The percentage of resveratrol and of oligomers in the crude extract closely depends on the type of vine used and, for a given type of vine on the extraction method and solvents used.

According to a particularly useful aspect, considering the enrichment in ORs that it allows to be attained, the crude extract is subjected to a purification stage by chromatography. An especially satisfactory technique corresponds to centrifugal partition chromatography (CPC). This technique is in particular described by A.P. FOUCAULT, Ed., Centrifugal Partition Chromatography, Chromatographic Science Series, Marcel Dekker Inc., 1995, 68, or W.D. CONWAY, Ed., Countercurrent Chromatography apparatus theory and applications, VCH Publishers Inc., 1990.

CPC is based on the partition of the solutes between two non-miscible liquid phases prepared by the mixture of two or more solvents or solutions. One of the two phases is kept stationary by a centrifugal force.

The solvents, their proportions and the flow rate chosen closely depend both on the stability of the stationary phase within the CPC column and the actual pressure.

High-performance results have been obtained with a hexane/ethyl acetate/ethanol/water mixture with for example the respective proportions of 6/48/11/42 or 4/5/3/3.

However, it is also possible to not use hexane or to replace at least one of said solvents with an equivalent solvent on the condition of modifying its proportions.

Therefore, hexane can be replaced by saturated, even unsaturated, hydrocarbons which are apolar and non-miscible with water, such as for example heptane, cyclohexane, or also chlorinated solvents such as chloroform.

Similarly, carbonylated or carboxylated solvents can be used instead of ethyl acetate, such as acetone, methylethylketone, methylisobutylketone, methylterbutylketone.

Alcohols other than ethanol can also be used in the mixture defined above, such as for example, methanol, n-propanol, propan-2-ol, n-butanol, butan-2-ol.

The water can be replaced, at least in part, even totally, by acetonitrile.

A person skilled in the art will therefore choose the most appropriate solvent or solvents depending on the nature of the purified extract subjected to CPC.

Thanks to the invention, crude extracts and enriched fractions are therefore available containing, as majority constituents, resveratrol and/or oligomers of the latter, as shown by the chromatographs which are referred to in the examples. These different extracts, namely crude or enriched also fall within the scope of the invention.

The implementation of additional separation stages by CPC allows isolation of these extracts enriched with resveratrol monomer on the one hand, and resveratrol in oligomer form on the other hand. These separations can be carried out on fractions enriched from a crude extract or on the crude extract itself by using mixtures of appropriate solvents according to the proportions which are suitable for the sought separation.

The derivatization of the ORs according to the invention allows products of great interest in numerous fields to be made available.

The presence of the introduced ester groups confers a stability as regards air and light to the resveratrol structures. In an advantageous manner, these groups are only eliminable when they are placed under conditions where these compositions must react, which allows the properties to be exploited, in particular the anti-radical and anti-oxidant properties of resveratrol, under optimum conditions.

The innocuity of the derivatives of the invention makes them particularly useful for all applications involving an administration or a use by man or animal.

The invention therefore relates to the use of the ester compositions defined above for the production of medicaments.

These medicaments can also contain other active ingredients, in particular products with a protective effect vis-à-vis oxidation reactions. For example β-carotene or vitamin E can be mentioned.

The pharmaceutical preparations produced according to the invention are in particular of use in anti-tumoral or vaso-protective treatments.

As forms of administration, the appropriate forms for the oral route are used, such as pills, tablets, gelatin capsules, or drops. These preparations advantageously contain approximately 50 to 200 mg of composition equivalent per unit dose preferably approximately 100 to 150 mg.

Other galenic forms are produced for an administration by cutaneous, sub-cutaneous, intradermic, intramuscular or intravenous route, in particular gels, solutions and others.

The compositions according to the invention can also be advantageously used for the production of cosmetic preparations.

These preparations are characterized in that they also contain at least one composition according to the invention in a proportion which allows an effective quantity of ORs to be made available, and comprising in combination the excipients allowing their application.

The liposoluble properties conferred on these preparations by the presence of the ester groups allow them to be easily incorporated with products used in a standard fashion in cosmetics.

The preparations according to the invention are presented in the form of cream, ointment, emulsion, gel, liposomes, lotion. They contain approximately 0.2 to 5% of active product.

The compositions according to the invention are also of use in the field of foods. The anti-radical properties of the ORs which they contain ensure better preservation of foods.

They can be used as additives for various products such as drinks and dairy products.

They can also be used in the form of pastes, granules or gels in various confectionery.

In these different applications, the cross-linked compositions according to the invention are moreover of use as vectors for active ingredients. These are retained in the spongy mass of the cross-linked compositions or are contained in the microcapsules.

The microcapsules can contain the active products in human or animal therapeutics, or can be used in the field of foods, in particular in dietetics.

Encapsulation allows the liposoluble or hydrosoluble character of the product to be ignored, and the various drawbacks which can be presented in the applications envisaged to be overcome. It also facilitates access to the site of action and allows the administration of the active ingredients which up to now would cause problems in this regard and/or provisionally protect them until they arrive at the site of action.

The invention will be illustrated hereafter by examples of the preparation of the esters of ORs and use for the production of medicaments and cosmetic preparations.

EXAMPLE 1

Extraction of ORs from Vine Stalks

The following protocols are implemented:

extraction by ultrasonic treatment

Vine stalks corresponding to a given type of vine are collected and, after they are washed and dried, they are subjected to a grinding stage.

400 to 1000 ml, for example 800 ml, of distilled water, and/or of one or more organic solvents are added to 100 g of stalk grounds.

For example, the following are used: water; water/acetone 3/2 or 1/1; methanol; ethanol; water/ethanol: 1/1; water/ethyl acetate: 1/1; ethanol/acetone: 1/1; water/ethanol/acetone: 2/1/1, 1/2/1 or 1/1/2

The mixture is subjected to ultrasonic treatment, generally operating for approximately 30 minutes to 3 hours.

The mixture is filtered, then concentrated.

Delipidation is carried out before or after this extraction stage. For this purpose, extraction is carried out using a solvent such as petroleum ether, hexane or chloroform.

This extract is in turn subjected to at least one other extraction stage. Ethyl acetate or ethyl ether is used at a rate of 3 to 5 times 100 ml.

The product obtained is then concentrated, taken up in water, lyophilized and stored in the form of a powder. A crude extract of ORs is thus available.

The anti-radical and antioxidant activity of the extracts obtained is checked in order to select operating conditions.

Figure 1:
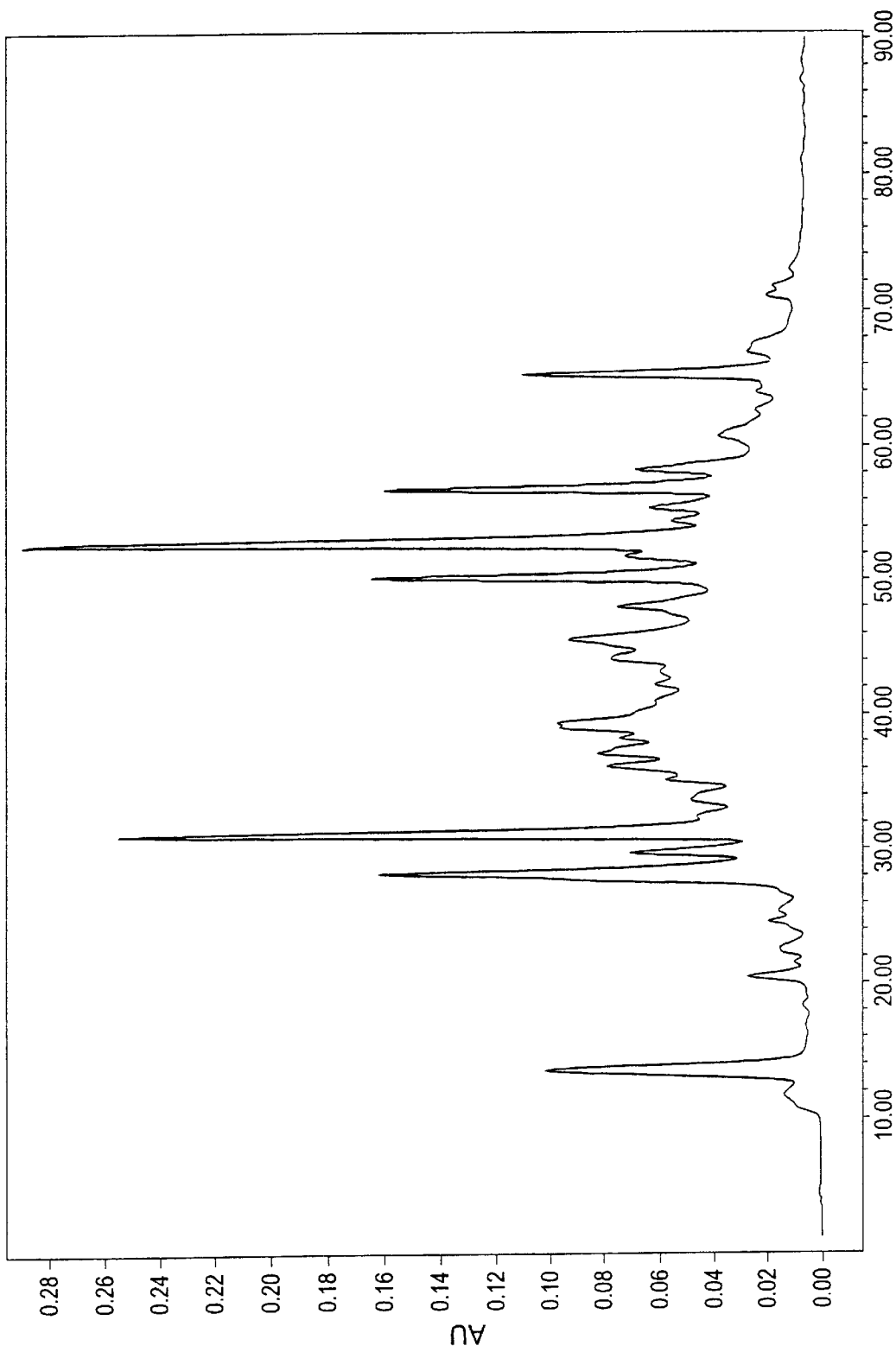
FIG. 1, high performance chromatography (HPLC) profile of extract of OR according to the invention.

FIG. 1 shows the HPLC chromatograph of an ethyl acetate extract obtained, after ultrasonic treatment for 2 hours, from 100 g of ground stalks (Merlot type) in 800 ml of water/acetone: 3/2, and delipidation with petroleum ether. Elution was carried out with A: $H_2O$/TFA; 100/0.0025 (TFA=trifluoroacetic acid) and B: MeOH/TFA 100/0.0025, according to the gradient

| min. | A | B |
|------|-----|-----|
| 0    | 100 | 0   |
| 120  | 0   | 100 | extraction by treatment with microwaves (800 to 900 W maximum)

As a variant, the operation is carried out as indicated above, but replacing the ultrasonic treatment with microwave treatment extraction by maceration-lixiviation Delipidation is carried out, under the conditions indicated above, before or after the maceration-lixiviation stage.

In an open column, 100 g of the vine stalk grounds is introduced, prepared as indicated above, then approximately 1 to 2 l of solvent.

Distilled water/organic solvent mixtures are used, such as for example a water/acetone mixture 3/2. The grounds/solvent mixture is left for 10 to 20 hours then the extract is recovered and concentrated to 100 ml in the case of an extract containing at least 100 ml of water, or to dryness in the case of an extract containing exclusively one or more organic solvents, the residue being taken up in 100 ml of water.

Delipidation is carried out before or after this extraction stage as described previously.

The extract obtained is then subjected to an extraction stage using ethyl acetate or ethyl ether as indicated previously for the preparation of extracts using ultrasonics or microwaves.

The yields of crude extracts prepared are most generally greater than 0.5% of the dry weight of the initial stalks, and can reach 1 to 1.5% according to the extraction conditions used and the origin of the stalks.

EXAMPLE 2

Obtaining OR-enriched Fractions by CPC

FIG. 1 shows the HPLC chromatograph of a crude extract, as obtained according to Example 1, containing a majority of resveratrol and catechin in practically equivalent proportions.

1 g of this extract, dissolved in 4 ml of stationary phase, is injected into CPC.

A SANKI device model LLB-M manufactured and marketed by the company Sanki Engineering (Kyoto, Japan).

Main Characteristics of the Device

Rotational speed: 0–2000 rpm

Column capacity: 230 ml

Maximum pressure: $60 \times 10^5$ Pa.

Rotor material: polyphenylenesulphide (PPS)

Partition disk: series of disks

Partition cell: 2136

Cell length: 15 mm.

The stationary and mobile phases are respectively the lower and upper phases recovered after agitation and decantation of the hexane/ethyl acetate/ethanol/water mixture: 6/48/11/42, given the implementation of the technique in ascending mode in this example.

The rotational speed is fixed at 1100 rpm, the flow rate at 2 ml/minute and the pressure is $34 \times 10^5$ Pa.

Figure 2:
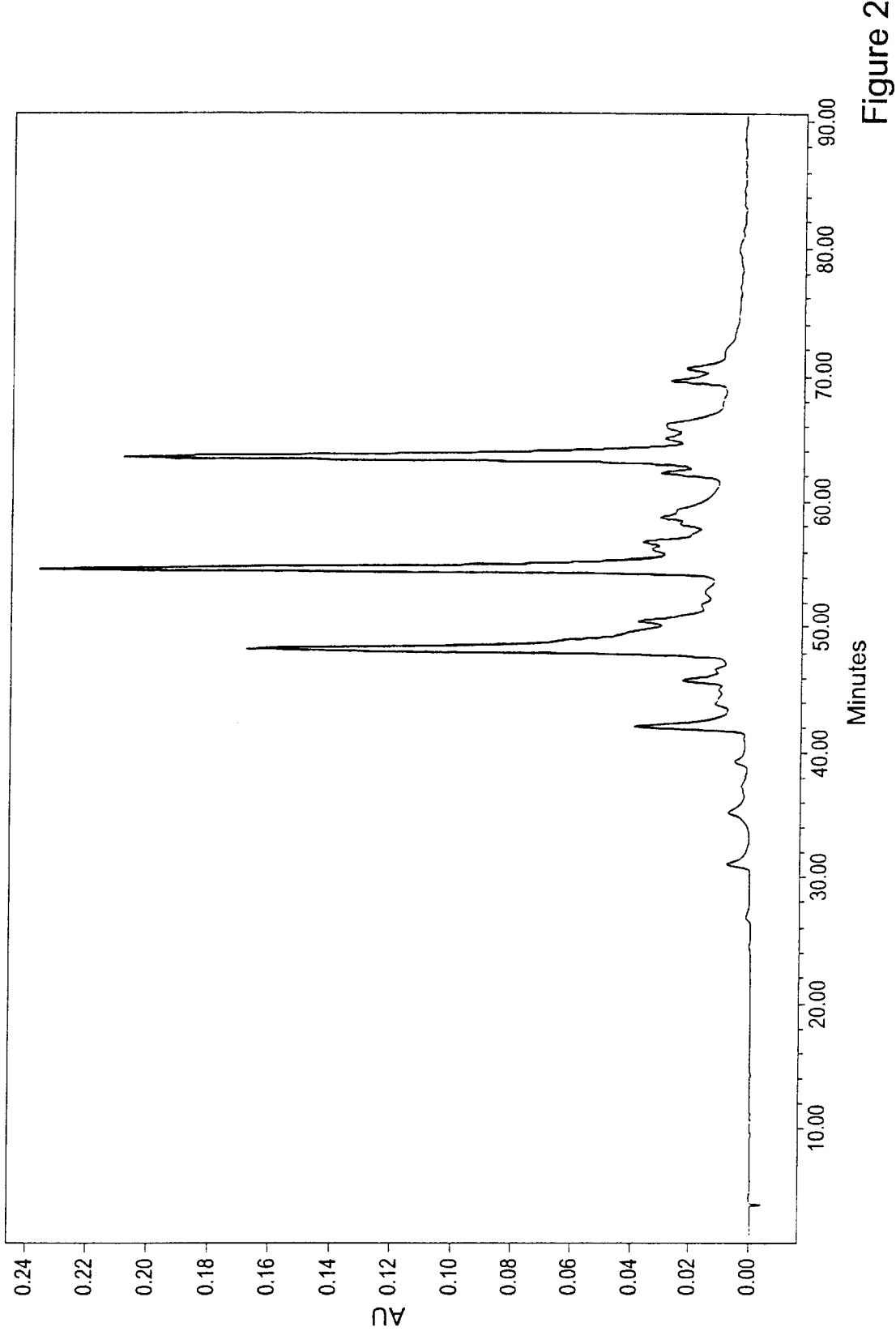
FIG. 2, high performance chromatography (HPLC) profile of extract of OR according to the invention.

Under these conditions, the fraction enriched in resveratrol and oligomers is collected rapidly, since the ORs are eluted during the first 30 minutes. FIG. 2 shows the HPLC chromatograph recorded from this fraction enriched in ORs. 120 mg of ORs is thus recovered, representing an enrichment of the order of 8.

EXAMPLE 3

Obtaining Monomer Resveratrol on the One Hand and Oligomer Forms on the Other Hand by CPC The 120 mg of ORs recovered in Example 2, dissolved in 2 ml of stationary phase, are separated in ascending mode. The stationary phase constitutes the lower phase of the hexane/ethyl acetate/ethanol/water mixture 4/5/3/3 and the mobile phase constitutes the upper phase of the same mixture. The rotational speed is 1100 rpm, the flow rate is 2 ml/minute and the pressure is $44 \times 10^5$ Pa. Under these conditions, the fraction enriched in resveratrol is collected after 150 minutes of elution and the fraction enriched in resveratrol oligomers is collected after 240 minutes.

The enrichments of the monomer resveratrol fractions on the one hand (7 mg) and of oligomers on the other hand (20.5 mg) are then respectively of the order of 17 and 6. A new enrichment in ORs of the order of 4.5 can be deduced. The enrichment relative to the initial crude extract is thus approximately 36.

HPLC analysis shows a percentage of resveratrol of the order of 81% ($t_R$ 55.6 minutes), i.e. 5.7 mg of pure resveratrol, as well as percentages in resveratrol oligomers of the order of 31% ($t_R$=48.5 minutes) and 53% ($t_R$=63.8 minutes), i.e. 17.2 mg of purified oligomers.

EXAMPLE 4

By applying the method described in Example 3 (duration of 4 hours) directly to the initial crude extract used in Example 2, it is possible to purify the resveratrol (8 mg) and the resveratrol oligomers (30 mg) in the same way.

The results originating from HPLC chromatographs are satisfactory. In fact, 2 fractions are obtained, one highly enriched in resveratrol ($t_R$=56.1 minutes) with a percentage of 74.0, the other highly enriched in resveratrol oligomers ($t_R$=48.9 minutes and $t_R$=64.2 minutes) with a percentage of 65.6.

EXAMPLE 5

Figure 3:
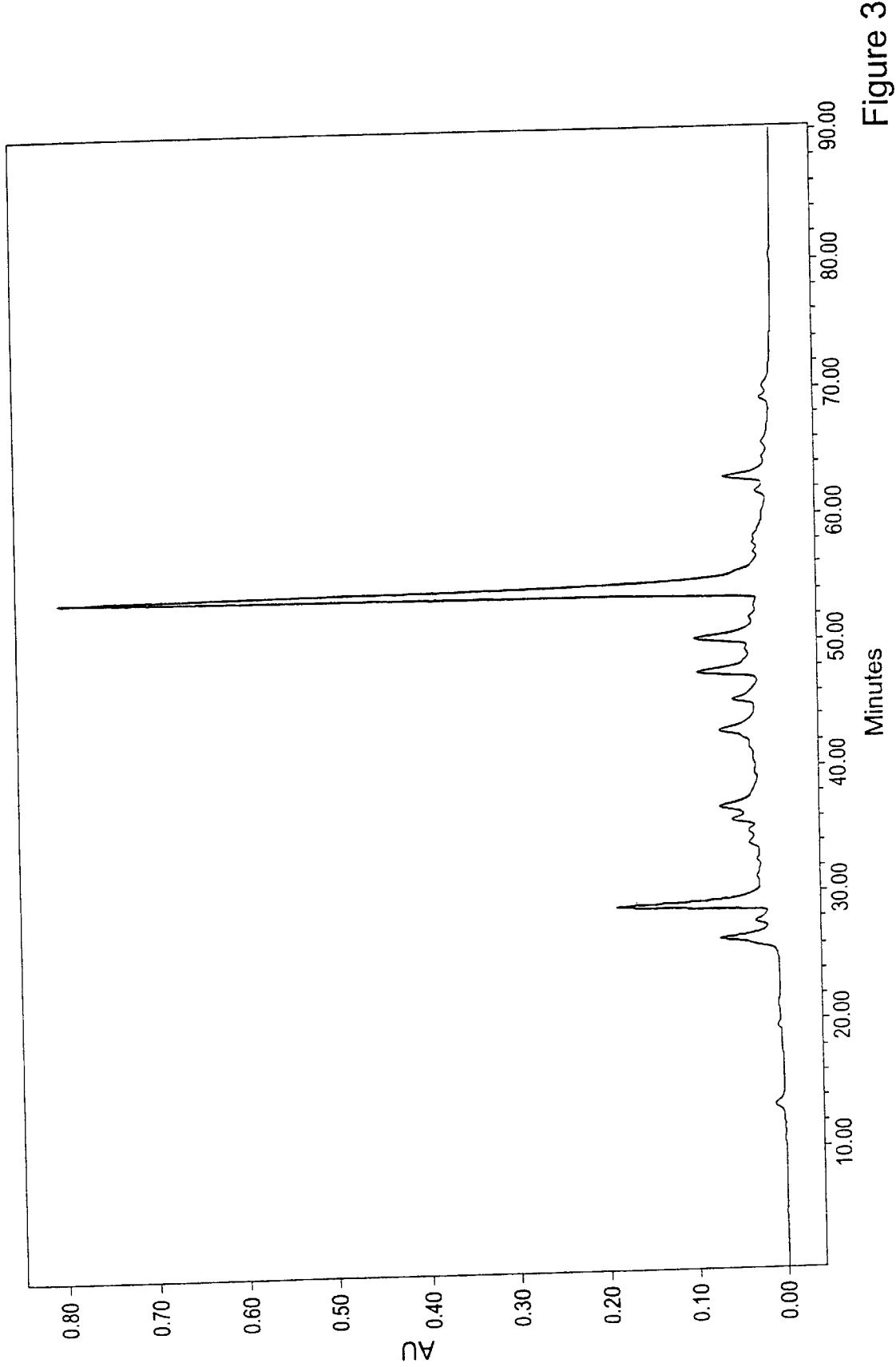
FIG. 3, high performance chromatography (HPLC) profile of extract of OR according to the invention.

Variant for Obtaining Fractions Enriched in ORs by CPC such as Obtained in Example 1, from a Crude Extract Containing a Majority of Resveratrol FIG. 3 represents the HPLC chromatograph of the crude extract of ORs before its study by CPC.

The separation conditions are identical to those described in Example 2.

Starting from 1 g of initial crude extract, 200 mg of enriched ORs is collected after 40 minutes, i.e. an enrichment factor equal to 5.

HPLC analysis of the corresponding enriched fraction shows a pourcentage of resveratrol ($t_R$=54.6 minutes) of 88%, i.e. 176 mg of pure resveratrol (enrichment factor of the order of 6).

EXAMPLE 6

Fractionation of the same initial crude extract (Example 5), according to the experimental protocol used in Example 3 above, allows an improved enrichment in pure resveratrol to be obtained.

Figure 4:
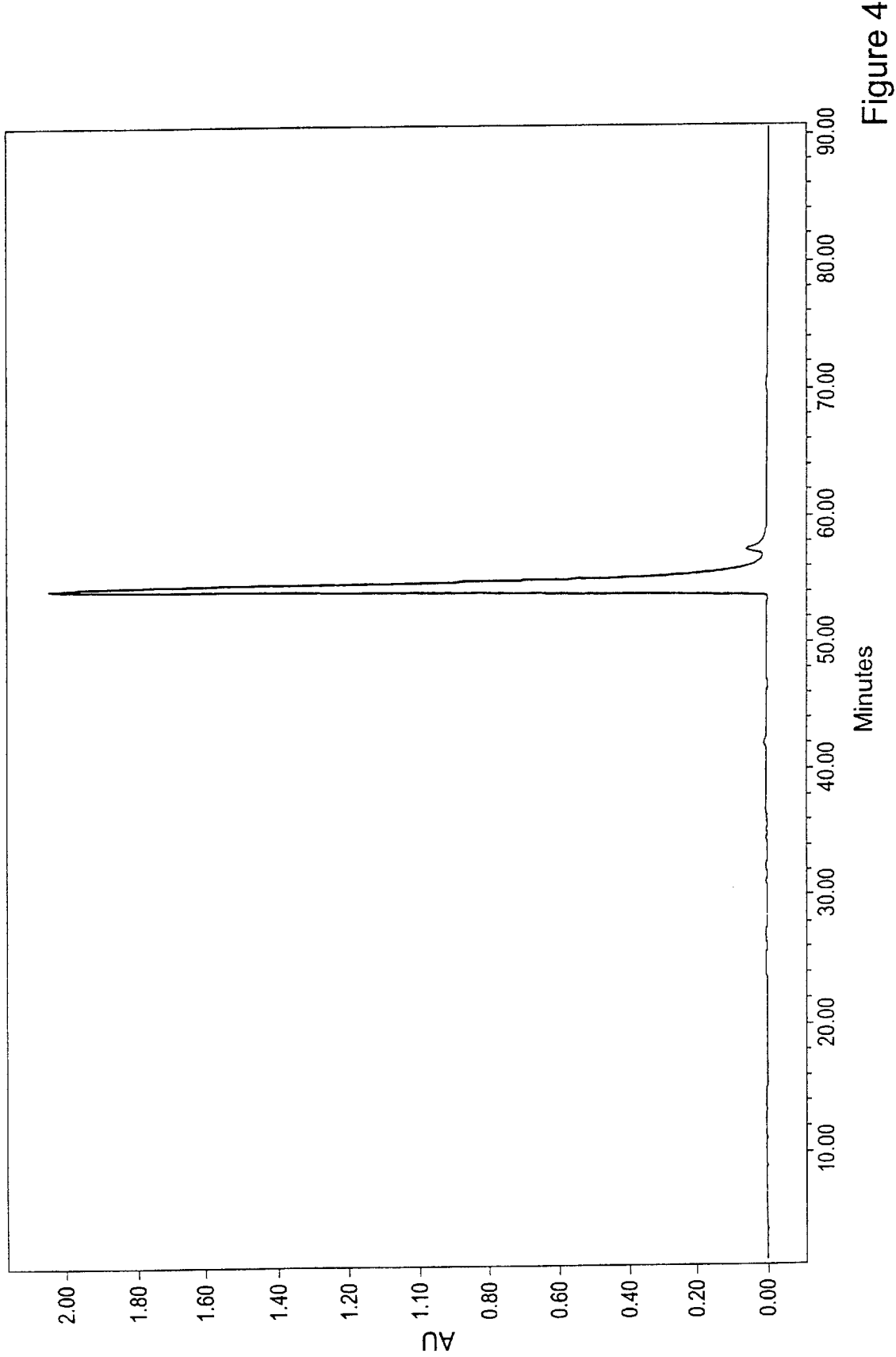
FIG. 4, high performance chromatography (HPLC) profile of extract of OR according to the invention.

In fact, the HPLC chromatograph (FIG. 4) shows a purity of the resveratrol thus obtained of 99% ($t_R$=54.4 minutes).

EXAMPLE 7

Synthesis the Perhexanoate of Resveratrol 0.09 ml of hexanoyl chloride (88 mg; $6.58 \times 10^{-4}$ mole; 10 eq.) is added, under agitation and dropwise, to 15 mg of resveratrol ($6.58 \times 10^{-5}$ mole) in solution in 2.5 ml of pyridine.

The reaction medium is agitated at ambient temperature, shielded from the air (under a slight nitrogen flow) and from the light, for 12 hours.

After concentration under reduced pressure, the residue is taken up in 20 ml of chloroform.

The organic phase is then washed twice with 50 ml of a 0.1 M HCl solution, twice with 50 ml of distilled water, twice with 50 ml of a solution of $Na_2CO_3$, then twice with 50 ml of distilled water.

This phase is dried over anhydrous $Na_2SO_4$, filtered through sintered glass no. 4, concentrated on a rotary evaporator and purified by preparative chromatography on a thick silica layer.

Figure 5:
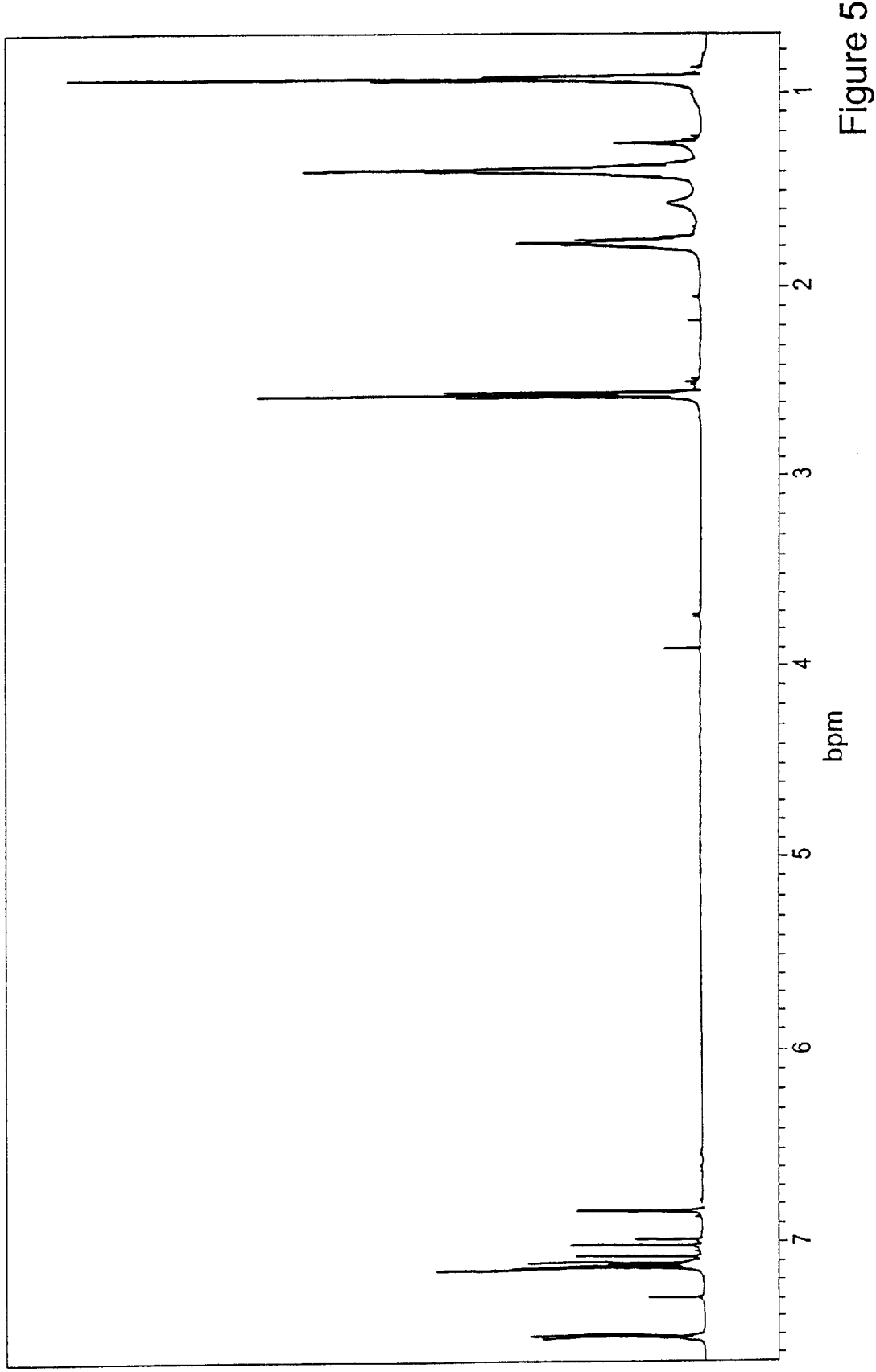
FIG. 5 the NMR $^1$H spectrum of resveratrol perhexanoate.

FIG. 5 shows the NMR $^1H$ spectrum.

Analyses of the IR, NMR $^1$H, and $^{13}$C spectra confirm that the sought ester has been obtained.

EXAMPLE 8

Synthesis of the Perpalmitate of ORs

A lyophilized extract of ORs (30 mg; $1.32 \times 10^{-4}$ mole) prepared according to Example 1, is dissolved in 5 ml of pyridine. 0.40 ml of palmitoyl chloride (0.36 g; $1.32 \times 10^{-3}$ mole; 10 eq.-resveratrol) is added dropwise to this solution.

The reaction mixture is left under agitation at 70° C., under a slight nitrogen flow and sheltered from the light, for 3 hours.

After concentration under reduced pressure, the residue is treated as in Example 7. The product thus obtained is checked by spectrometry.

EXAMPLE 9

Synthesis of the Perhexanoate of ORs

The protocol described in Example 8 is applied using 200 mg of lyophilized extract of ORs ($8.77 \times 10^{-4}$ mole) and 1.23 ml of hexanoyl chloride (1.18 g; $8.77 \times 10^{-3}$ mole; 10 eq.-resveratrol).

Analysis by IR and NMR $^1$H spectrometry confirms that the sought ester has been obtained.

EXAMPLE 10

Synthesis of the Perbutyrate of ORs 25 ml of dichloromethane is added under vigorous agitation to 250 mg of the lyophilized extract of ORs prepared according to Example 1 ($1.10 \times 10^{-3}$ mole), dissolved in 5 ml of distilled water.

25 ml of a 5% buffered aqueous solution of sodium hydrogen phosphate (pH # 10), 37 mg of tetra-butylammonium hydrogen sulphate are then added.

($1.10 \times 10^{-4}$ mole; 1/10 eq.-resveratrol) and 0.57 ml of butyryl chloride (0.58 g; $5.48 \times 10^{-3}$ mole; 5 eq.-resveratrol).

The reaction mixture is left under vigorous agitation for 45 minutes.

At the end of the reaction, the organic phase is recovered and washed twice with 15 ml of distilled water, then evaporated under reduced pressure and purified by preparative chromatography on a thick layer of silica.

The product thus obtained is checked by spectrometry.

EXAMPLE 11

Synthesis of the Perlaurate of ORs 1.32 g of lauric acid ($6.58 \times 10^{-3}$ mole; 6 eq.-resveratrol) in solution in 20 ml of 1,2-dichloroethane is added to a lyophilized extract of ORs (250 mg; $1.10 \times 10^{-3}$ mole), prepared according to Example 1.

Then 1.36 g of dicyclocarbodiimide (DCC) ($6.58 \times 10^{-3}$ mole; 6 eq.-resveratrol) is dissolved in 5 ml of 1,2-dichloroethane and thus added to the solution previously prepared. 97 mg of 4-pyrrolidinopyridine ($6.58 \times 10^{-4}$ mole; 6/10 eq. resveratrol) dissolved in 1 ml of 1,2-dichloroethane is then added.

The reaction mixture is left under agitation for 2 hours, at ambient temperature, under a slight nitrogen flow and sheltered from the light.

The organic phase is then filtered and concentrated under reduced pressure.

The residue is then taken up in 25 ml of hexane. The hexane solution is filtered, then washed twice with 50 ml of a 0.1 M soda solution, then twice with 50 ml of distilled water. The organic phase is then concentrated with a rotary evaporator.

The product obtained in this way is analyzed by spectrometry.

EXAMPLE 12

Synthesis of the Persorbate of ORs

The protocol described in Example 11 is applied using 250 mg of lyophilized extract of ORs ($1.10 \times 10^{-3}$ mole) and 0.74 g of sorbic acid ($6.58 \times 10^{-3}$ mole; 6 eq.-resveratrol) and chloroform as organic solvent.

EXAMPLE 13

Preparation of Microcapsules of ORs cross-linked by Terephthaloyl Chloride.

A lyophilized extract of ORs (50 mg; $2.19 \times 10^{-4}$ mole), prepared according to Example 1, is dissolved in 5 ml of a 5% solution of sodium hydrogen phosphate (pH # 10).

This solution is emulsified in 20 ml of a 5% chloroform solution of sorbitan trioleate (Span 85®) by agitation at 3000 rpm for 5 minutes.

The cross-linking agent, terephthaloyl chloride (89 mg; $4.39 \times 10^{-4}$ mole; 2 eq.-resveratrol), in solution in 15 ml of chloroform, is then added to the emulsion.

Agitation is maintained for 30 minutes. At the end of reaction, the reaction mixture is centrifuged.

The solid interface is recovered, resuspended in 30 ml of chloroform and centrifuged again.

The operation is repeated once with chloroform and twice with distilled water. The centrifugation pellet is recovered and resuspended in 5 ml of distilled water. The microcapsules thus prepared are dried by lyophilization and checked by light-optical microscopy.

EXAMPLE 14

Preparation of Microcapsules of ORs Cross-linked by Sebacoyl Chloride

The protocol described in Example 13 is applied using 50 mg of lyophilized extract of ORs ($2.19 \times 10^{-4}$ mole) and 0.09 ml of sebacoyl chloride (0.10 g; $4.38 \times 10^{-4}$ mole; 2 eq.-resveratrol).

EXAMPLE 15

Preparation of Microcapsules of ORs Cross-linked by Adipoyl Chloride

The protocol described in Example 13 is applied using 50 mg of lyophilized extract of ORs ($2.19 \times 10^{-4}$ mole) and 0.06 ml of adipoyl chloride (80 mg; $4.38 \times 10^{-4}$ mole; 2 eq.-resveratrol).

EXAMPLE 16

Cosmetic Sun Protection Preparation

A sun protection emulsion with skin anti-aging properties is produced by mixing a sun filter with an ester prepared according to the invention and excipients for cream.

Example of formulation:

Neo Heliopan E $_{1000}{}^R$
(isopropylmethoxycinnamate and ethyldiisopropylcinnamate) . . . 3%

Perlaurate of ORs according to Example 6 . . . 3%

Excipients for W/O cream . . . qs
Composition of excipients:
- Propylene glycol dicaprylate/dicarate
+ stearalkonium hectorite+ propylene carbonate (Miglyol 840 gel B®) . . . 20.0%
Bis-diglyceryl caprylate/caprate/isostearate/hydroxystearate/adipate (Softisan 649®) . . . 5.0%
Isostearyl diglyceryl succinate (Imwitor) 780 K® . . . 5.0%
Paraffin oil . . . 8.0%
Solid paraffin . . . 3.0%
Magnesium sulphate . . . 2.0%
Water . . . sqf 100%

EXAMPLE 17

Preparation of Gelatin Capsules for use in Dietetics

Perlaurate of ORs prepared according to Example 11 is mixed with selenium and vitamin E;
Perlaurate of ORs: 85 mg (corresponding to 25 mg of ORs),
DL- α-tocopherol acetate: 40 mg,
Selenium: 50 mg

EXAMPLE 18

Preparation of Phlebotonic and Vascular Protective Medicament

Gelatin capsules are prepared from 230 mg of perhexanoate of ORs (corresponding to 100 mg of ORs), prepared according to Example 9, and excipients for a gastro-resistant coating, such as cellulose acetophthalate.

EXAMPLE 19

Preparation of a Buccal Gel for Use in Radiotherapy

The following composition is formulated:
2% Carbopol$^R$ gel 934 P . . . 89.85 g
Methyl parahydroxybenzoate containing soda . . . 0.13 g
Para propyl hydroxybenzoate containing soda . . . 0.02 g
Labrafil R . . . 5 g
Perhexanoate of ORs prepared according to Example 9 . . . 5 g
(corresponding to 2.2 g of ORs)

What is claimed is:

1. Esters of resveratrol comprising monomers and/or oligomers wherein, the monomers comprise at least one ester group of formula —O—CO—A, and the oligomers are formed from monomer units joined by carbon-carbon bonds, or other, and/or monomers cross-linked by —O—CO—R—CO—O— groups, wherein,
   A represents an alkyl radical with at least two carbon atoms, linear or branched, saturated or unsaturated, an aryl radical, except for the phenyl radical in the case of a resveratrol monomer, aralkyl or aralkylene, and
   R represents an alkylene radical with 0 to 10 carbon atoms, saturated or unsaturated, and/or; arylene radical having 1 to 3 rings and/or a heterocyclic radical, and the diastereoisomers of these units.

2. Esters according to claim 1, comprising monomer and/or oligomer esters with at least one —O—CO—A— group.

3. Esters according to claim 2, wherein A represents a saturated or unsaturated fatty acid radical, selected from the group comprising butyric; valeric, hexanoic, sorbic, lauric; palmitic; stearic, oleic, linoleic; linolenic, linolenic, arachidonic, eicosapentaenoic, docosahexanoic acid.

4. Esters according to claim 1, comprising cross-linked monomers and/or oligomers using CO—R—CO bridges where R represents an alkylene radical with 0 to 10 carbon atoms, saturated or unsaturated, and/or an arylene radical comprising 1 to 3 rings and/or heterocyclic radical.

5. Esters according to claim 4, wherein R is a radical of a diacid chosen from the acid groups comprising: malic, malonic, glutaric, phthalic, a chloride of diacids, an anhydride, or an isocyanate.

6. Esters according to claim 4, which are in the form of microcapsules.

7. Esters according to claim 4, which are in the form of a spongy mass.

8. Process for obtaining esters of resveratrol, comprising the reaction of monomers and/or oligomers of resveratrol with as acylation agents the compounds of formula A—CO—O—A1, or A1-O—CO—R—CO—-O—A1, where
   A represents an alkyl radical with at least two carbon atoms, linear or branched, saturated or unsaturated, an aryl, aralkyl or aralkylene radical,
   R represents an alkylene radical with 0 to 10 carbon atoms, saturated or unsaturated, and/or l arylene radical having 1 to 3 rings and/or a heterocyclic radical, and
   A1 represents a hydrogen atom, a halogen atom, a C1 to C8 alkyl radical, or aryl, a —C—A group or isocyanate, A and A1 not being able to represent respectively a phenyl radical and a chlorine atom in A—CO—O—A1.

9. Process according to claim 8, wherein the esterification is carried out according to the Schotten Baumann reaction, in alkaline aqueous medium.

10. Process according to claim 8 wherein when the acylation agents are used, an emulsion of (O/W) type is formed by dispersion, under agitation, of an alkaline, aqueous solution of the monomers and/or oligomers or resveratrol in an organic solvent which is not miscible with water, then the cross-linking agent, A1-O—CO—R—CO—O—A1 in solution in said non-miscible organic solvent is added, or, as a variant, an emulsion of (O/W) type is formed by dispersion, under agitation, of an organic solution containing said cross-linking agent in an aqueous solution of monomers and/or oligomers of resveratrol, with an alkaline agent in aqueous solution added to it to adjust the pH of the dispersing phase to approximately 9–11.5.

11. Process according to claim 8, wherein the monomers and/or oligomers of resveratrol used are as those obtained by extraction using water and/or an organic solvent from vine stalks.

12. A method for preparing cosmetics or dietetics comprising using the esters according to claim 1 in admixture with one or more active ingredients.

13. A method for preparing a medicament, comprising using esters according to claim 1 in admixture with one more active ingredients.

14. Esters according to claim 5, wherein said chloride of diacids are selected from the group comprising terephthaloyl dichloride, succinyl dichloride, sebacoyl dichloride and adipoyl dichloride.

15. Esters according to claim 5, wherein said isocyanate is selected from the group comprising toluene or hexamethylene diisocyanate.

* * * * *